(12) United States Patent
Rau et al.

(10) Patent No.: US 10,441,377 B2
(45) Date of Patent: Oct. 15, 2019

(54) SURGICAL GUIDANCE DEVICE AND METHOD FOR ITS PREPARATION

(71) Applicant: MEDIZINISCHE HOCHSCHULE HANNOVER, Hannover (DE)

(72) Inventors: Thomas Stephen Rau, Langenhagen (DE); Omid Majdani, Hannover (DE); Thomas Lenarz, Hannover (DE); Luder Alexander Kahrs, Hannover (DE)

(73) Assignee: Medizinische Hochschule Hannover, Hannover (DE)

( * ) Notice: Subject to any disclaimer, the term of this patent is extended or adjusted under 35 U.S.C. 154(b) by 236 days.

(21) Appl. No.: 15/546,146

(22) PCT Filed: Feb. 9, 2016

(86) PCT No.: PCT/EP2016/052707
§ 371 (c)(1),
(2) Date: Jul. 25, 2017

(87) PCT Pub. No.: WO2016/131675
PCT Pub. Date: Aug. 25, 2016

(65) Prior Publication Data
US 2018/0008367 A1    Jan. 11, 2018

(30) Foreign Application Priority Data
Feb. 18, 2015 (EP) .................................... 15155574

(51) Int. Cl.
*A61B 17/17* (2006.01)
*A61B 17/34* (2006.01)
(Continued)

(52) U.S. Cl.
CPC .............. *A61B 90/11* (2016.02); *A61B 17/17* (2013.01); *A61B 17/3403* (2013.01);
(Continued)

(58) Field of Classification Search
CPC ................................. A61B 90/11; A61B 17/17
See application file for complete search history.

(56) References Cited

U.S. PATENT DOCUMENTS

| 6,572,624 B2 * | 6/2003 | U .......................... A61B 90/11 606/130 |
| 7,981,122 B2 | 7/2011 | Labadie et al. |
| 2013/0211424 A1 | 8/2013 | Thiran et al. |

FOREIGN PATENT DOCUMENTS

| WO | 2004/021898 A1 | 3/2004 |
| WO | 2009/047494 A1 | 4/2009 |
| WO | 2013/043640 A1 | 3/2013 |

* cited by examiner

*Primary Examiner* — Christian A Sevilla
(74) *Attorney, Agent, or Firm* — W&C IP

(57) ABSTRACT

The invention is related to a surgical device for patient-specific guidance of at least one tool used during a surgical intervention, comprising at least the following features: a) at least one carrier system which is arranged for fixation on a bone structure of a patient, b) at least one guiding system connectable to the carrier system, the at least one guiding system comprising at least one base module and at least one guiding part for precisely defined guidance of at least one tool used during the surgical intervention, c) at least one connecting means for establishing a mechanical connection between the at least one guiding part and the at least one base module, wherein the connecting means comprises at least a non-fixed operating state and a fixed operating state, wherein in the non-fixed operating state the at least one guiding part can be adjusted relative to the base module in a patient-specific adjustment and in the fixed operating state the at least one guiding part is mechanically fixated relative to the at least one base module in the patient-specific adjustment, d) at least one mechanical interface for connecting the carrier system to the guiding system, comprising first interface means of the carrier system and second interface (Continued)

Figure 1:
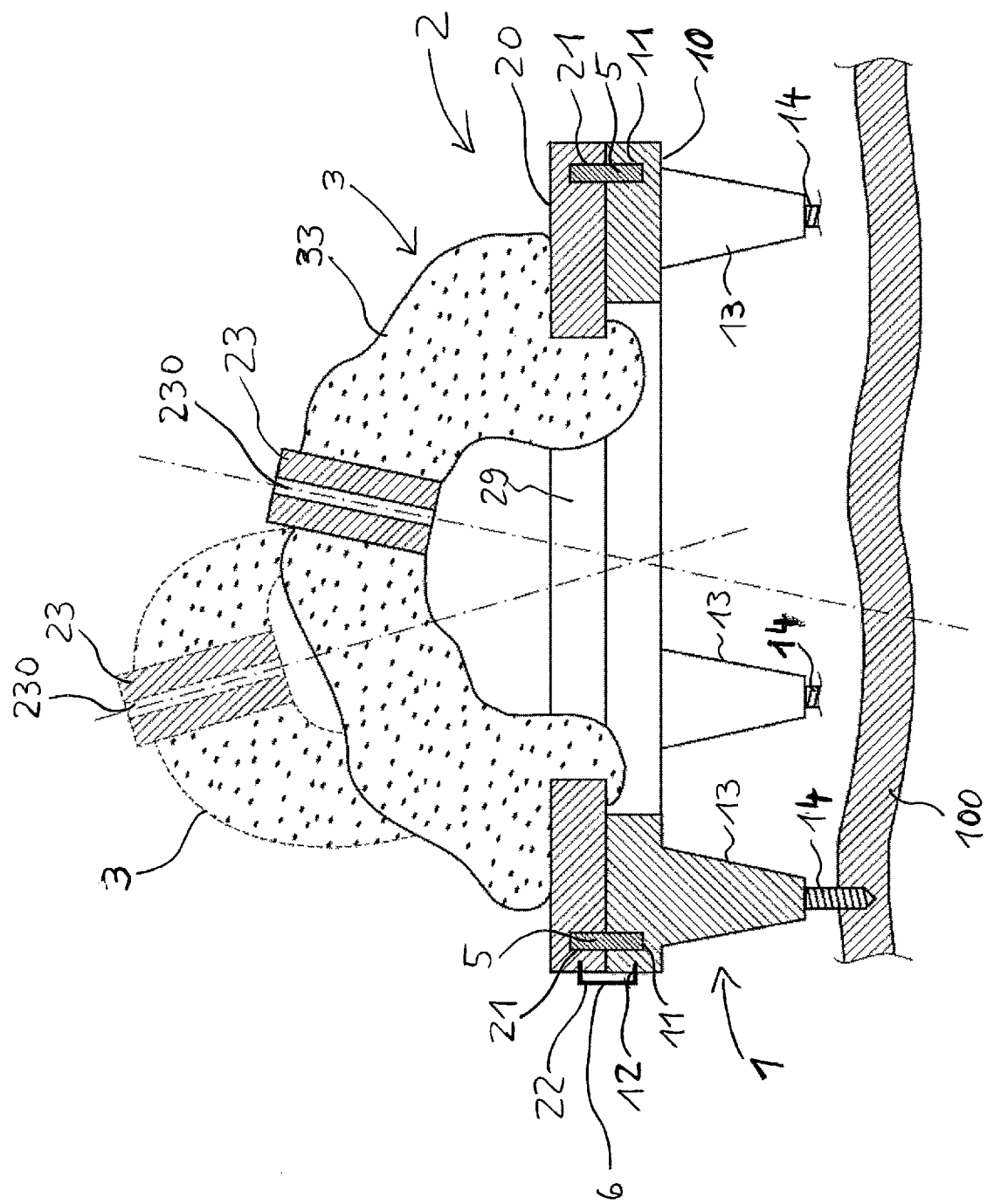

means of the guiding system, wherein the first interface means can be connected via form fit with the second interface means, thereby ensuring a defined adjustment of the guiding system relative to the carrier system by means of form fit. The invention is further related to a method for preparation of such a surgical guidance device.

14 Claims, 19 Drawing Sheets

(51) Int. Cl.
*A61B 90/11* (2016.01)
*A61B 17/56* (2006.01)
*A61B 34/10* (2016.01)
*A61B 17/00* (2006.01)

(52) U.S. Cl.
CPC ............... *A61B 2017/00526* (2013.01); *A61B 2017/3407* (2013.01); *A61B 2017/568* (2013.01); *A61B 2034/108* (2016.02)

SURGICAL GUIDANCE DEVICE AND METHOD FOR ITS PREPARATION

The invention is related to a surgical guidance device for patient-specific guidance of at least one tool used during a surgical intervention. The invention is further related to a method for preparation of such a surgical guidance device.

In several areas of surgical interventions the precise guidance of surgical tools is required. For example, for cochlea implantation the precise guidance of a surgical drill is required. For deep brain stimulation a precise electrode guidance is necessary. There are already existing proposals using automatic navigation and/or robotic support. In addition, so called mini- or micro-stereotactic solutions were proposed. In such proposals, some kind of frame is used for guidance of the surgical tool. The frame is fixated on a bone structure of a patient. Such proposals are disclosed in U.S. Pat. No. 7,981,122 B2 or U.S. 2013/0211424 A1.

It is an object of the present invention to provide a surgical guidance device for patient-specific guidance of at least one tool used during surgical intervention which is further optimized regarding ease of use, in particular with regard to the duration of the surgical intervention. It is another object of the invention to propose a method for preparation of such a device.

This object is achieved by a surgical device for patient-specific guidance of at least one tool used during a surgical intervention, comprising at least the following features:
a) at least one carrier system which is arranged for fixation on a bone structure of a patient,
b) at least one guiding system connectable to the carrier system, the at least one guiding system comprising at least one base module and at least one guiding part for precisely defined guidance of at least one tool used during the surgical intervention,
c) at least one connecting means for establishing a mechanical connection between the at least one guiding part and the at least one base module, wherein the connecting means comprises at least a non-fixed operating state and a fixed operating state, wherein in the non-fixed operating state the at least one guiding part can be adjusted relative to the base module in a patient-specific adjustment and in the fixed operating state the at least one guiding part is mechanically fixated relative to the at least one base module in the patient-specific adjustment,
d) at least one mechanical interface for connecting the carrier system to the guiding system, comprising first interface means of the carrier system and second interface means of the guiding system, wherein the first interface means can be connected via form fit with the second interface means, at least in part, thereby ensuring a defined adjustment of the guiding system relative to the carrier system by means of form fit.

The present invention allows for significantly reducing the total amount of time for a surgery. This has advantages both for the personal performing the surgery and for the patient. The duration of anaesthesia can be shortened. The surgical intervention can be done without interruptions, e.g. with only one anaesthesia of the patient.

A further advantage is that the parts of the surgical guidance device as well as any support tools can be provided as premanufactured sterile parts. In particular, the parts can be provided as one time usable parts which are disposed after the surgical intervention. Because the invention allows for shortening the total length of the surgical intervention, there is also no need for additional sterilisation of the parts since they are used only during one intervention without interruption.

In the fixed operating state the connecting means fixate the guiding part relative to the base module in a rigid and durable manner, allowing no significant deviation from the patient-specific adjustment. On the other hand, the non-fixed operating state allows for relatively easy change of the position and/or orientation of the guiding part relative to the base module. In particular, the adjusting process can be done manually or with automatic actuation means. In any case the required forces are relatively low.

The patient-specific adjustment can be an adjustment with regard to the three-dimensional spatial position (x/y/z) and/or the orientation. If both position and orientation can be adjusted, than the so-called pose of an object can be adjusted relative to another object. Any of these combinations is referred to by the term patient-specific adjustment.

When the connecting means are to be transformed from the non-fixed operating state into the fixed operating state, this can be done by chemical, biological and/or physical means, in particular by mechanical means. For example, the connecting means can be a combination of a multiaxially modifiable mechanical unit together with a chemical glue which is applied to the mechanical unit. The glue can be e.g. a rapid hardening glue, like CA glue. The fixation can also be done solely by mechanical means, e.g. by use of a clamping screw or the like. Further, the connecting means may comprise a magnetorheological liquid. The connecting means can then be transformed from the non-fixed operating state into the fixed operating state by applying a magnetic field to the magnetorheological liquid. Also, any other liquid like e.g. water can be used. In such case a transformation from the non-fixed state into the fixed state can be done by cooling the liquid below its freezing point. Further, the fixed operating state can be achieved by applying underpressure, e.g. by means of a vacuum suction device.

It is advantageous to use a material which is already approved and is e.g. a standard material for surgical interventions, like bone cement, to constitute at least a part of the connecting means. This has the advantage that no unusual substance is required which is normally not used in surgery. In particular, such material can be provided in sterile form.

In such way the invention has great potential to be accepted immediately by operating room personal. Especially the well-known bone cement enables operating room use without further investigations.

Compared to proposals using rapid prototyping methods, the present invention pro-vides for a better acceptability to the medical personal, since complicate equipment which is normally not used in surgery can be avoided.

The connecting means can be one time transformable (irreversibly transformable) from the non-fixed operating state into the fixed operating state or they can be reversible from the fixed operating state into the non-fixed operating state or any other state which is not the fixed operating state. If irreversibly transformable connecting means are applied, then any inadvertent misadjustment of the surgical guidance device can be reliably avoided. Therefore, a higher degree of safety is achieved.

According to an advantageous embodiment of the invention, the at least one connecting means comprises at least a modifiable material with figurine and/or plastic properties, which is in the non-fixed operating state manually deformable and allows a patient-specific adjustment of the at least one guiding part relative to the at least one base module wherein the deformable material can be rapidly hardened and/or cured, for transforming the connecting means into the fixed operating state. In this embodiment, the connecting means may comprise as a modifiable material e.g. bone cement, a dental casting compound, a polyester mixture, gypsum, plasticine, a freezable liquid and/or a magnetorheological liquid. This has the advantage that the connecting means can be manually formed, like a modelling clay, and can then be hardened and/or cured. Such modifiable material allows the user a lot of freedom in modifying the material and achieving the patient-specific adjustment. The hardening and/or curing can be done by a chemical reaction, like it happens with a one or two component potting compound. The hardening and/or curing can also be done by a physical process, like freezing and/or applying a magnetic field, electric or electromagnetic field, or through radiation with light (e.g. ultraviolet, infra-red).

According to an advantageous embodiment of the invention, the at least one guiding system comprises at least one reception chamber for reception of the modifiable material. This has the advantage that the modifiable material is less likely to get into contact with undesired regions of the surgical guidance device during preparation of the device. Any undesired fixations through the modifiable material can be better avoided. For example, the reception chamber can be part of the base module and/or the guiding part.

According to an advantageous embodiment of the invention, the at least one base module is connected via one or more deformable and/or flexible hose-like coupling means with the at least one guiding part, wherein the interior of one or more hose-like coupling means forms a reception chamber for reception of the modifiable material. This has the advantage that the modifiable material can be completely encapsulated within the hose-like coupling means and therefore provides a very clean solution for applying the modifiable material. The hose-like coupling means can be designed like a concertina, e.g. in the form of corrugated bellows. It is advantageous to place at least three hose-like coupling means with equidistant angular positions on the base module and the guiding part. Of course, it is also possible to use more or less than three hose-like coupling means, and it is also possible to distribute them irregularly on these parts.

According to an advantageous embodiment of the invention, the at least one connecting means comprises an articulated mechanical connection part. The articulated mechanical connection part can be fixated in the patient-specific adjustment by a mechanical fixation device, e.g. a clamping screw, and/or by chemical means, e.g. by applying glue or the mentioned modifiable material. The articulated mechanical connection part can be a material bonded connection or any other type of connection, like a hinge, a cardanic connection, a ball/ball socket connection.

The connecting means can comprise, e.g. in addition to the aforementioned parts, strengthening elements e.g. in the form of wires, spirals, springs or a hinged bracket. In this way, the connecting means can be further mechanically strengthened like an armouring, as it is done with ferroconcrete. For example, such strengthening elements can be integrated into a hose-like coupling means.

According to an advantageous embodiment of the invention, the guiding part is adjustable via the at least one connecting means relative to the base module in at least five degrees of freedom, when the at least one connecting means is in the non-fixed operating state.

According to an advantageous embodiment of the invention, by means of the articulated mechanical connection part the freedom of movement of the at least one guiding part relative to the at least one base module is reduced by at least one or at least two degrees of freedom, when the at least one connecting means is in the non-fixed operating state. By such limitation of the freedom of movement the adjustment process is simplified for the user. The remaining degrees of freedom are still sufficient for reaching the desired patient-specific adjustment.

According to an advantageous embodiment of the invention, the at least one guiding part is adjustable via the articulated mechanical connection part relative to the base module in four or five degrees of freedom, when the at least one connecting means is in the non-fixed operating state.

According to an advantageous embodiment of the invention, the at least one connecting means is transformable from the non-fixed operating state into the fixed operating state in less than one hour. According to further advantageous embodiments, the connecting means is transformable from the non-fixed operating state into the fixed operating state in less than 30 minutes, or in less than 15 minutes, or in less than one minute. With such improvements the required waiting periods during a surgical intervention are minimized. Therefore, the impact on the patient and the operating personal is also minimized.

According to an advantageous embodiment of the invention, the at least one guiding part comprises a guiding channel for guiding a surgical drill or other medical instruments, like an insertion tool for a cochlea implant, a stimulation electrode, a biopsy needle. Through such a guiding channel, e.g. in the form of cylindrical tubular channel, the precision of guiding of the surgical drill or other medical instrument can be improved.

According to an advantageous embodiment of the invention, the carrier system and/or the guiding system is made of material which is not disturbing for radiological and similar imaging procedures, like computer tomography, cone beam computer tomography, magnetic resonance imaging.

According to an advantageous embodiment of the invention, the surgical guidance device further comprises a manufacturing system in the form of a separate tool. The manufacturing system comprises a holder for holding the base module, wherein the holder comprises a third interface means, wherein the third interface means can be connected via form fit to the second interface means, at least in part, thereby ensuring a defined adjustment of the guiding system relative to the holder by means of form fit. This has the advantage that the adjusting procedure for achieving the patient-specific adjustment can be done separately, when the guiding system is not mounted on the carrier system respectively on the patient. By such means the impact on the patient can be further minimized. Another advantage is that by means of the separate manufacturing system the adjustment procedure can be improved. The manufacturing system can be equipped with precise mechanical adjustment means, e.g. in the form of fine pitch thread in connection with step motors. Further, the complete adjustment procedure together with the transformation of the connecting means into the fixed operating state can be done on the manufacturing system.

By designing the third interface means compatible to the second interface means, or at least to a part of the second interface means, for example by making them the same as the first interface means, the guiding system with the already patient-specifically adjusted and fixated guiding part can be transferred from the manufacturing system to the carrier system. Through the form fit connection of the mechanical interface the same patient-specific adjustment is guaranteed when the guiding system is connected to the carrier system.

It is possible that the third interface means mechanically interact with all of the second interface means to establish the form fit connection. It is also possible that the third interface means interact only with a part of the second interface means, for establishing the form fit connection. In particular, it is also advantageous to establish the form fit connection between the guiding system and the carrier system using one part of the second interface means, and to establish the form fit connection between the guiding system and the holder by another part of the second interface means. Of course, it is also advantageous to use the same part of the second inter-face means for establishing each of the form fit connections.

According to an advantageous embodiment of the invention, the manufacturing system comprises a retaining part for retaining the at least one guiding part. This has the advantage that the guiding part can be fixated on the manufacturing system separately from the base module. The base module can be held by the holder, while the guiding part is held independently by the retaining part.

According to an advantageous embodiment of the invention, the manufacturing system comprises adjustable positioning means, which allow to adjust the retaining means and/or the holder relative to each other, in order to adjust a guiding part retained by the retaining means relative to a base module held by the holder in the desired patient-specific adjustment. The positioning means may act on the retaining means, thereby changing the adjustment of the guiding part, or on the holder, thereby changing the adjustment of the base module, or on both. It is important that any combination is possible which allows relative positioning of the retaining means and the holder relative to each other, in order to achieve the desired patient-specific adjustment of the guiding part relative to the base module.

The manufacturing system may also comprise at least one coordinate-measuring machine, a navigation system and/or a 3D-printer.

The actuation means of the manufacturing system can be automatically computer controllable actuation means, e.g. by electric motors, or they can be manually adjustable. If they are manually adjustable, the personal doing the surgical intervention have to perform the correct adjustment. For easing and supporting this manual adjustment, adjustment data may be calculated and provided by a computer, based on measurements done on the patient, e.g. by use of computer tomography. For ex-ample, the adjustment can be precisely done by using micrometer calliper in the actuation system of the manufacturing system.

An automatic positioning of the guiding part in the patient-specific adjustment can also be done by using roboter arms in the manufacturing system.

In case a manual adjustment of the guiding part is implemented, this can be supported by a coordinate measuring machine which allows a precise measuring of the adjustment, namely the position and orientation, of the guiding part relative to the base module on the manufacturing system. As further alternatives, any other electromechanical, stereo-optical or electromagnetic navigation system can be used for manual adjustment.

As a further alternative, the manufacturing system can be patient-specifically produced, e.g. by means of a generative manufacturing method, e.g. using a 3D printer. In this way, the patient is first scanned e.g. by use of computer tomography, and the resulting data are used for producing a patient-specific manufacturing system which comprises a dummy carrier system being an exact copy of the original carrier system. Further, the desired trajectory which shall be achieved by the guiding system is already reproduced within the manufacturing system, e.g. in the form of a cylindrical bore. With such a manufacturing system it is possible to perform the patient-specific adjustment of the guiding system by mounting the guiding system through the de-fined mechanical interface to the manufacturing system and to use a support tool, like the aforementioned retaining part, for adjusting the guiding part relative to the base module. The cylindrical retaining part is than lead through the guiding channel and the cylindrical bore in the manufacturing system, which automatically brings the guiding part in the patient-specific adjustment. This positioning can then be frozen by transforming the connecting means into the fixed operating state.

The guiding system may comprise further mechanical elements, like e.g. an adapter, e.g. in the form of a wedge, between the carrier system and the base module. This allows to change the angle of the trajectory of the carrier system. This may be helpful if the manufacturing system cannot reach the desired patient-specific adjustment, e.g. due to mechanical restrictions. In such cases through such an adapter the limitations of the manufacturing system may be overcome with little overhead.

The object of the invention is further achieved by a method for preparation of a device of the aforementioned kind, wherein intraoperatively the at least one guiding part is adjusted relative to the at least one base module in the patient-specific adjustment and is then fixated in the patient-specific adjustment through transforming the connecting means from the non-fixed operating state into the fixed operating state. By such preparation method the aforementioned advantages of the surgical guidance device can also be achieved. The term "intraoperatively" means that the preparation method can be performed and finalized in the time duration of a surgical intervention, in particular during a surgical intervention without an interruption of the anaesthesia of the patient.

Further "intraoperatively" may also cover that the preparation method is performed only in a sterile environment, e.g. in the surgery room (or rooms).

According to an advantageous embodiment of the invention, the at least one guiding part is adjusted relative to the at least one base module by means of a manufacturing system and is mechanically supported by the manufacturing system at least until the transformation of the connecting means into the fixed operating state is finished to the extent that the at least one guiding part is fixated relative to the at least one base module in the patient-specific adjustment.

According to an advantageous embodiment of the invention, the at least one guiding system is removed from the manufacturing system and is mounted to the carrier system via the mechanical interface for connecting the carrier system with the guiding system, after the at least one guiding means is fixated relative to the at least one base module in the patient-specific adjustment.

According to an advantageous embodiment of the invention, the method for preparation of the surgical guidance device is completely performed under sterile conditions.

The invention is further described by means of examples using several drawings.

The drawings show:
FIGS. 1 to 5 a first embodiment of the invention and
FIGS. 6 to 8 a second embodiment of the invention and
FIGS. 9 to 16 a third embodiment of the invention and
FIGS. 17 to 19 a fourth embodiment of the invention.

In the drawings same numerals are used for the same elements.

In the first embodiment depicted in FIGS. 1 to 5 the surgical guidance device comprises a carrier system 1 and a guiding system 2. The carrier system 1 comprises a plate like mounting structure 10 for receiving the guiding system 2 on the carrier system 1. On its lower side the mounting structure 10 is equipped with rigid mounting legs 13. Via the mounting legs 13 the carrier system 1 can be rigidly fixated, e.g. by means of screws 14, to a bone structure 100 of the patient.

The guiding system 2 comprises a base module 20 which can have a plate like shape as depicted in the figures. The guiding system 2 further comprises a guiding part 23, e.g. in the form of a sleeve, which has a central guiding channel 230 which supports a precisely defined guidance of at least one tool during the surgical intervention, for example a surgical drill. The guiding part 23 is mounted to the base module 20 by means of a modifiable material 33 which acts as the connecting means 3 for establishing a mechanical connection between the guiding part 23 and the base module 20. The modifiable material 33 can e.g. be bone cement. As can be seen, the material 33 bridges the relatively large gap between the guiding part 23 and the base module 20.

The base module 20 as well as the mounting structure 10 may comprise a central opening 29 in the area where the tool used during the surgical intervention is guided through the guiding channel 230.

FIG. 1 shows in broken lines an alternative patient-specific adjustment of the guiding part 23 via the connecting means 3 relative to the base module 20.

In order to ensure a defined adjustment of the guiding system 2 relative to the carrier system, a form fit connection between the base module 2 and the carrier system 1, in particular the mounting structure 10, is provided. This is achieved by a mechanical interface between these parts, comprising first interface means 11, 12 of the carrier system and second interface means 21, 22 of the guiding system, providing for a form fit connection between the two parts. For example, the first and second inter-face means may comprise precision bore holes which are connected to each other by a dowel pin 5. In addition, a clamping connection via an external clamp 6 may be added. The clamp 6 is inserted into clamping holes in the base module 20 and the mounting structure 10, acting as first interface means 12 and second interface means 22.

Figure 2:
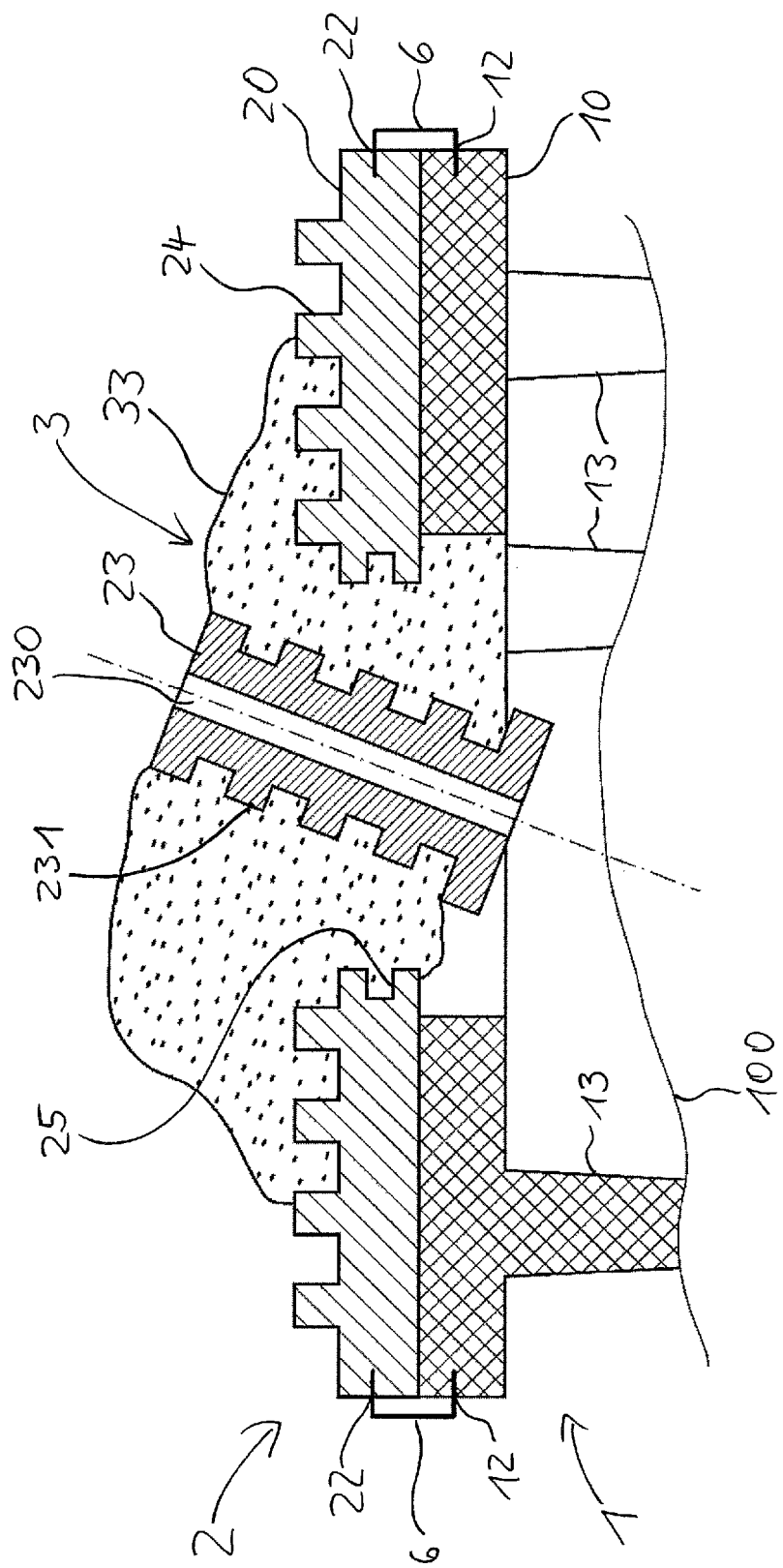

FIG. 2 shows generally the same arrangement as depicted in FIG. 1, but with some further improvements regarding the robustness of the mechanical connection between the guiding part 23 and the base module 20 via the modifiable material 33. The outer surface of the guiding part 23 may be provided with an uneven regular or irregular structure 231, which improves the gripping forces to the encircling material 33. Similarly, the outer surfaces of the base module 22 which may come into contact with the material 33 may also comprise an uneven structure 24, 25, for improving gripping forces between the material 33 and the base module 20.

Figure 3:
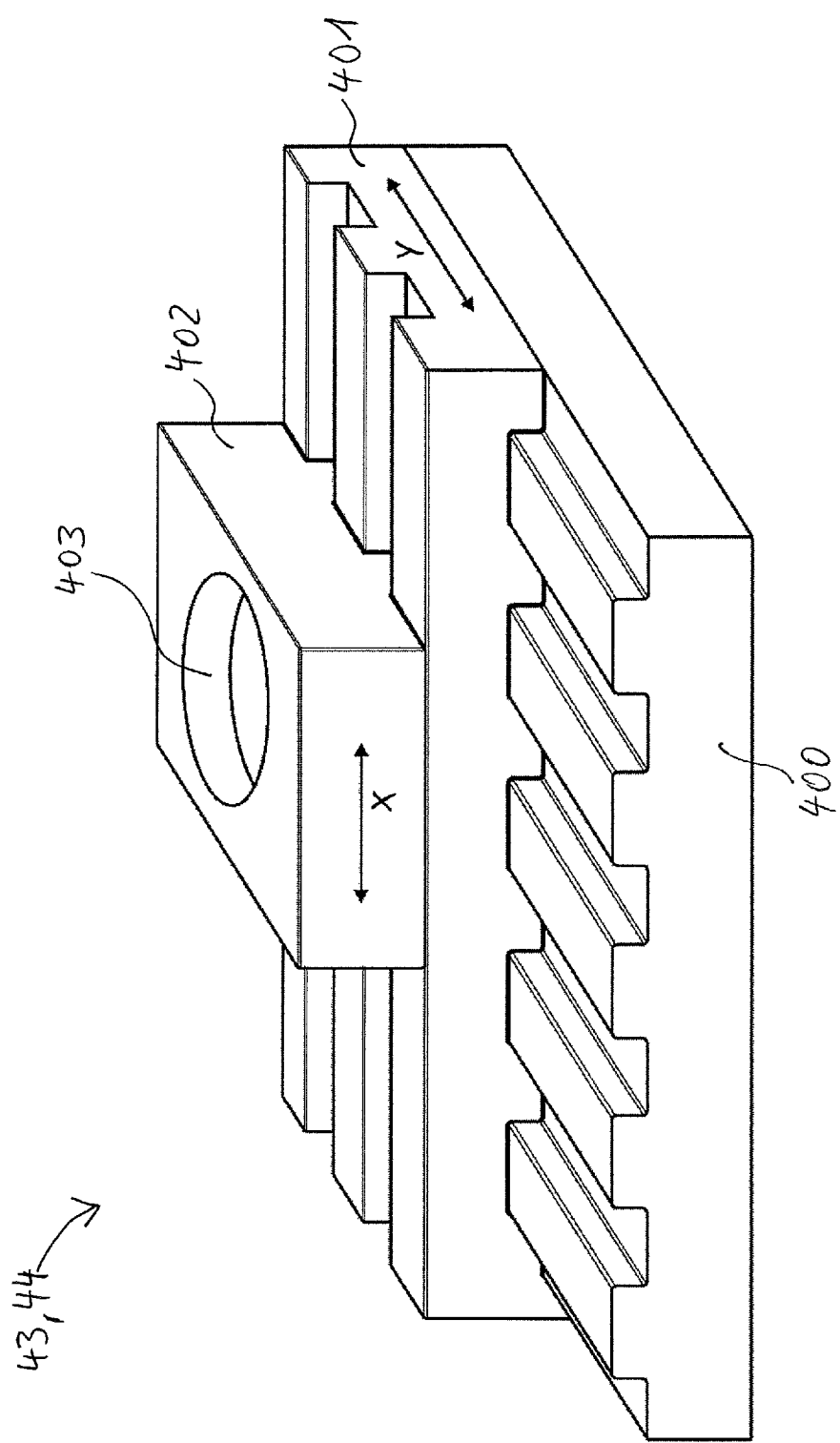

FIG. 3 shows an example of an x-y-actuator which allows for linear movement of an actuator head 402 relative to an actuator basis 400. A linear shift unit 401 can be linearly shifted relative to the actuator basis 400 in the y coordinate direction. The actuator head 402 can be linearly shifted relative to the shift unit 401 in the x coordinate direction. For mounting purposes, the actuator head 402 may comprise a fixation hole 403. The x-y-actuator depicted in FIG. 3 is used as actuation units 43, 44 in the manufacturing system 4 depicted in FIGS. 4 and 5.

Figure 4:
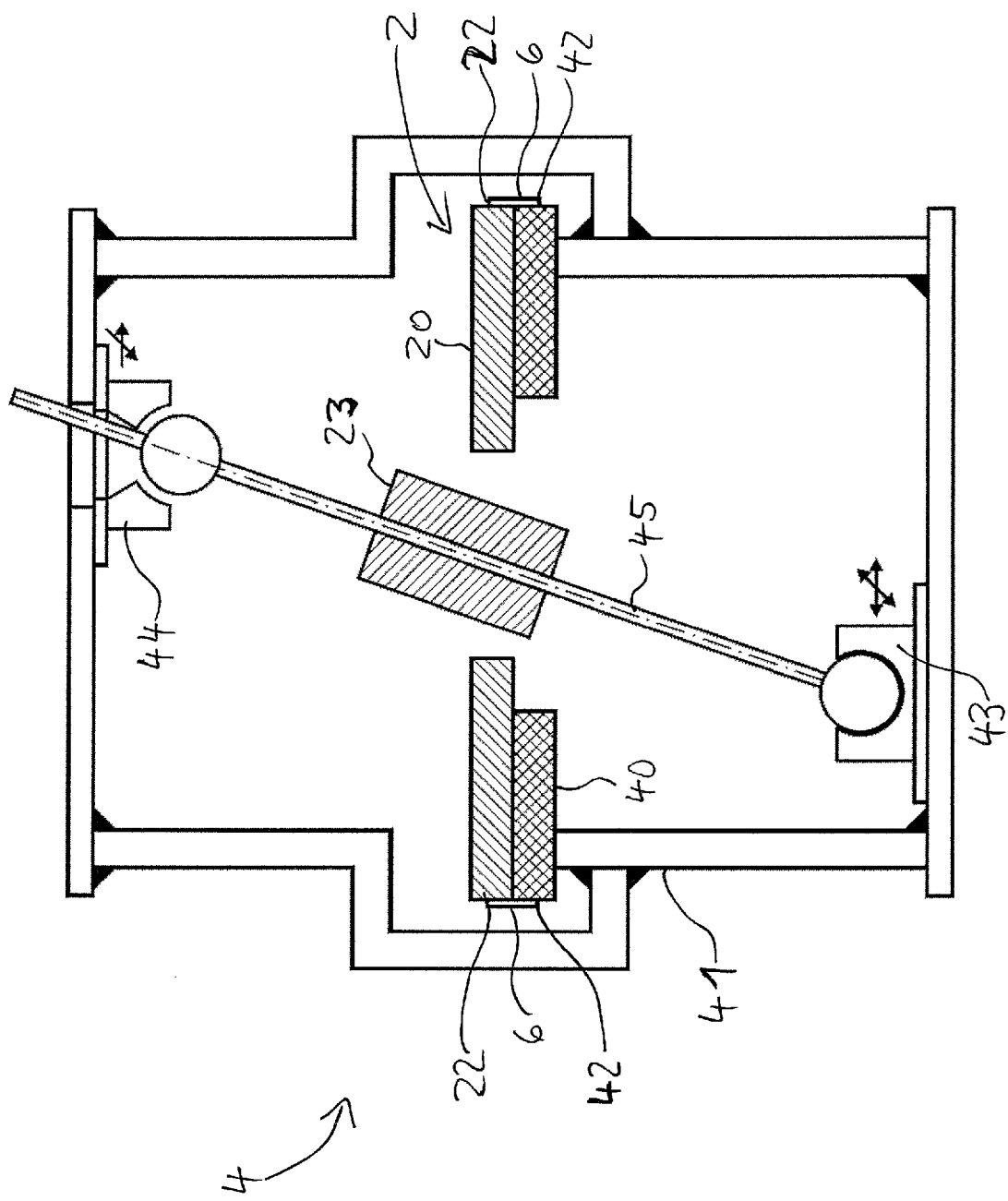

FIG. 4 shows a manufacturing system 4 which is used for preparation of the guiding system 2, namely for adjusting the guiding part 23 relative to the base module 20 in a patient-specific adjustment and for fixing these parts relative to each other in this patient-specific adjustment. For this purpose, the base module 20 is mounted to a holder 40 of the manufacturing system 4. The holder 40 comprises third interface means 42, which are compatible with the second interface means of the base module 20, or in other words, the holder 40 comprises the same interface means as the carrier system 1. This allows for transferring the properly adjusted guiding system to the carrier system mounted on the bone structure of a patient, while ensuring that the patient-specific adjustment prepared in the manufacturing system is exactly re-produced on the carrier system 1.

As can be seen, the holder 40 is fixated on a frame structure 41 of the manufacturing system 4. The frame structure 41 comprises a lower actuating unit 43 and an upper actuating unit 44, the actuating units 43, 44 being for example x-y-actuators shown in FIG. 3. The guiding part 23 is retained by a retaining part 45, which e.g. can be a rod which is pushed through the guiding channel 230 of the guiding part 23. The retaining part 45 may comprise additional fixation means, e.g. in the form of a thread and nuts mounted on the thread, for positioning and holding the guiding part 23 at a desired position on the retaining part 45.

By means of x-y-movement of the actuating units 43, 44 the guiding part 23 is then brought into the desired patient-specific adjustment. The required data for controlling the actuation units 43, 44 in a way that the patient-specific adjustment is reached can be produced by first examining the patient, e.g. by means of computer tomography. The computer tomography data can be computed into the necessary control data for the actuating units 43, 44.

Figure 5:
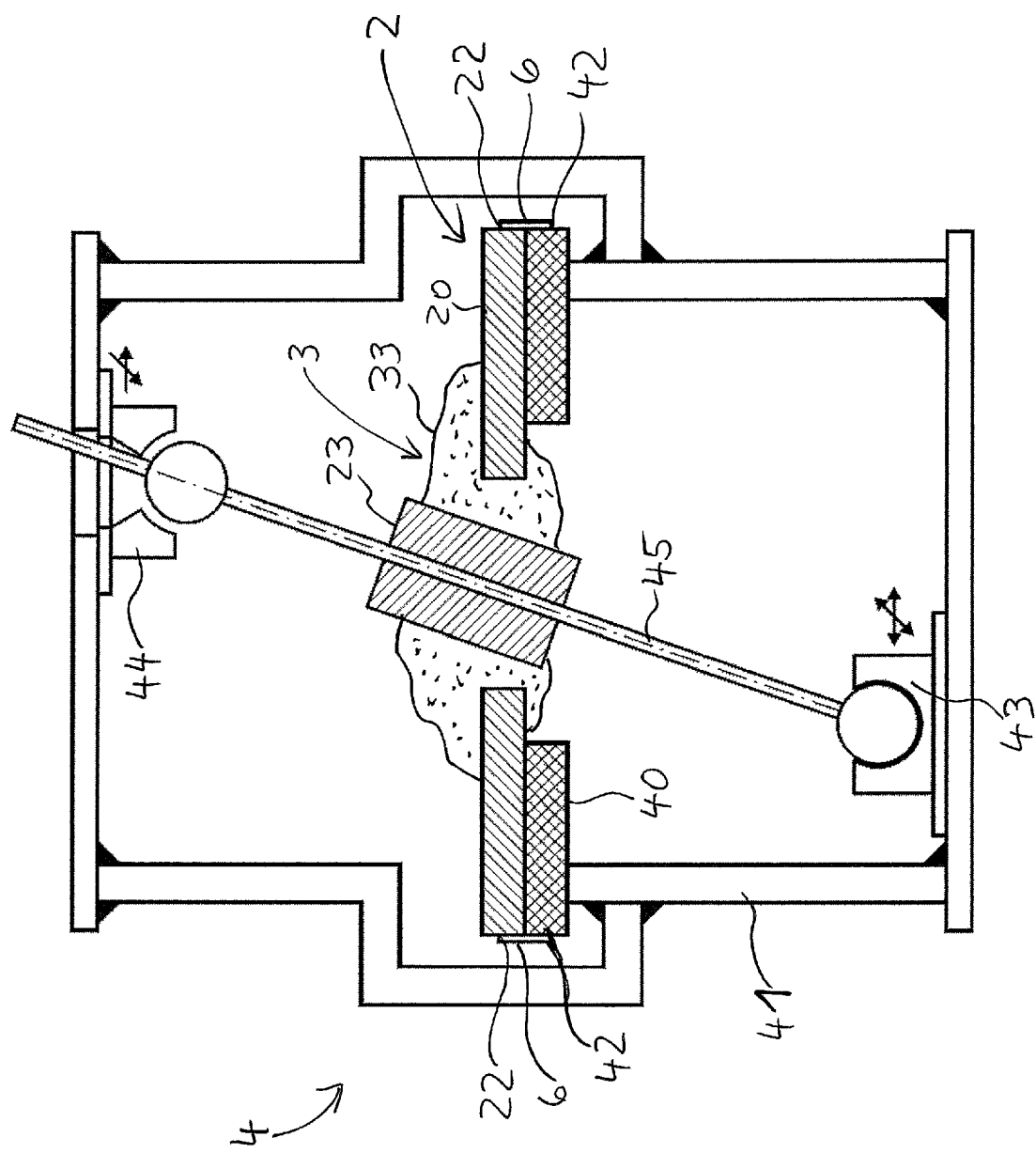

Then, the modifiable material 33 is applied, as it is shown in FIG. 5. The modifiable material 33 is then hardened, which means that the connecting means 3 which are established by the material 33 are then transformed from the non-fixed operating state into the fixed operating state. It is also possible to apply the modifiable material 33 before the final patient-specific adjustment is reached, because the modifiable material allows in the non-fixed operating state such modifications.

Figure 6:
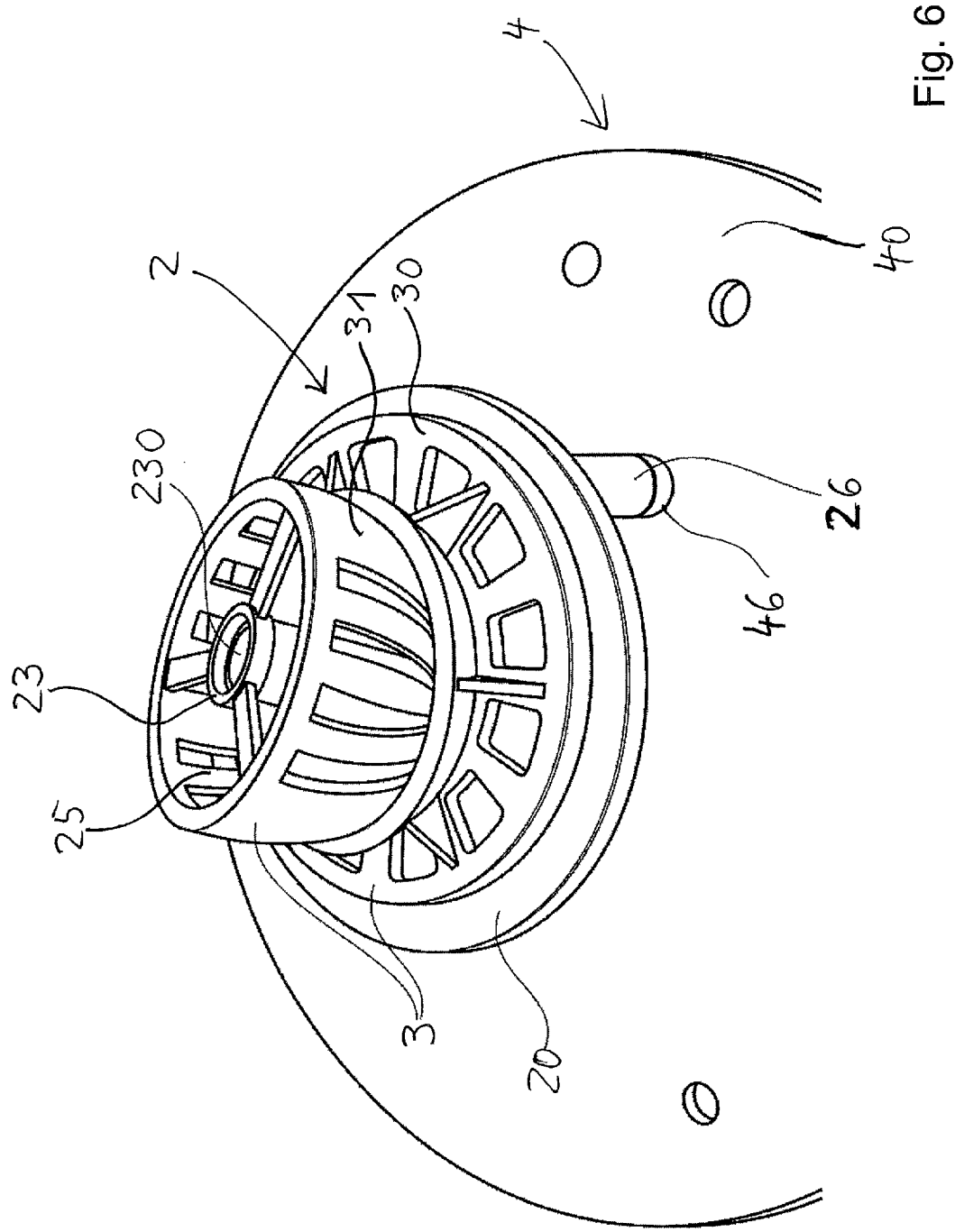
Figure 7:
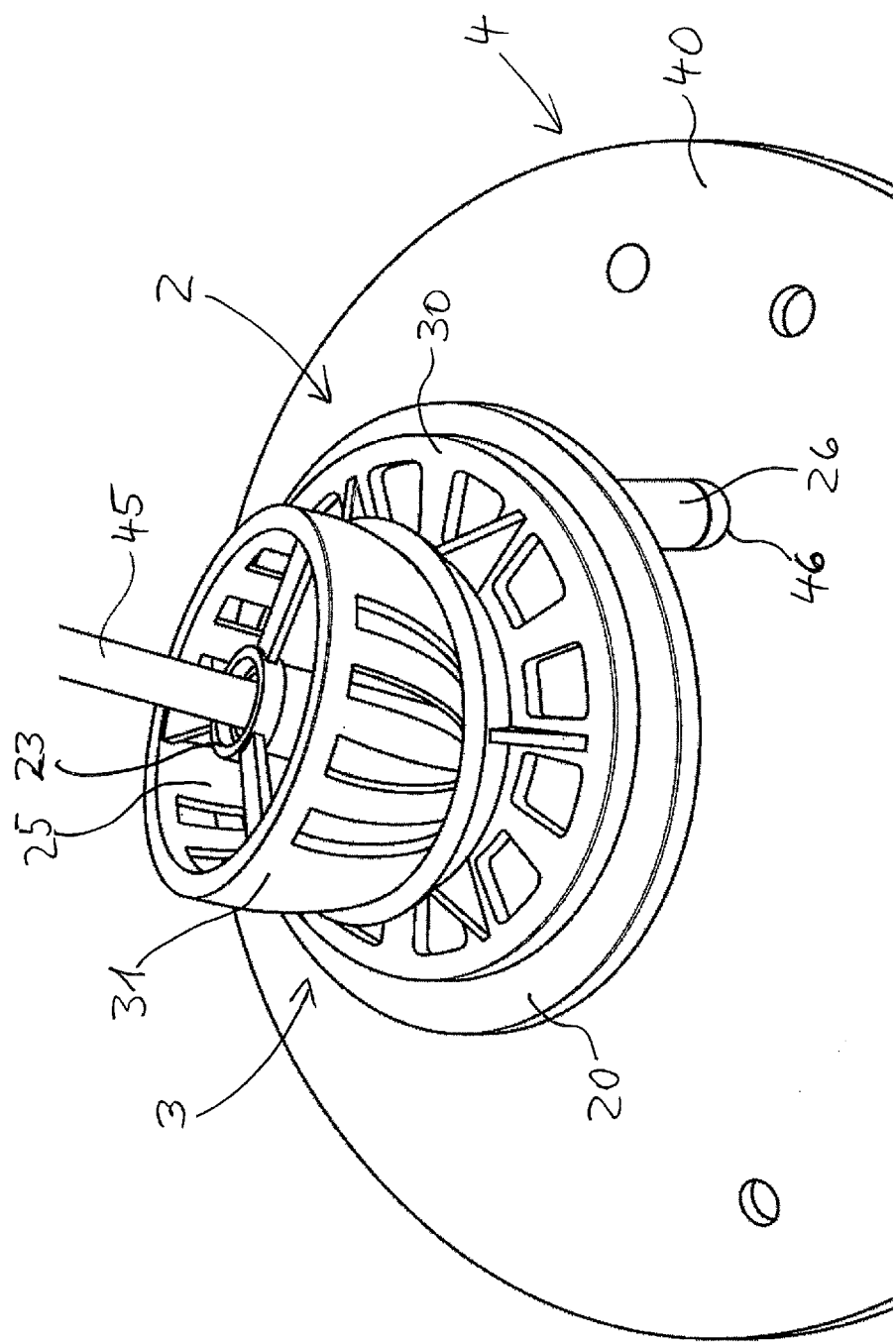
Figure 8:
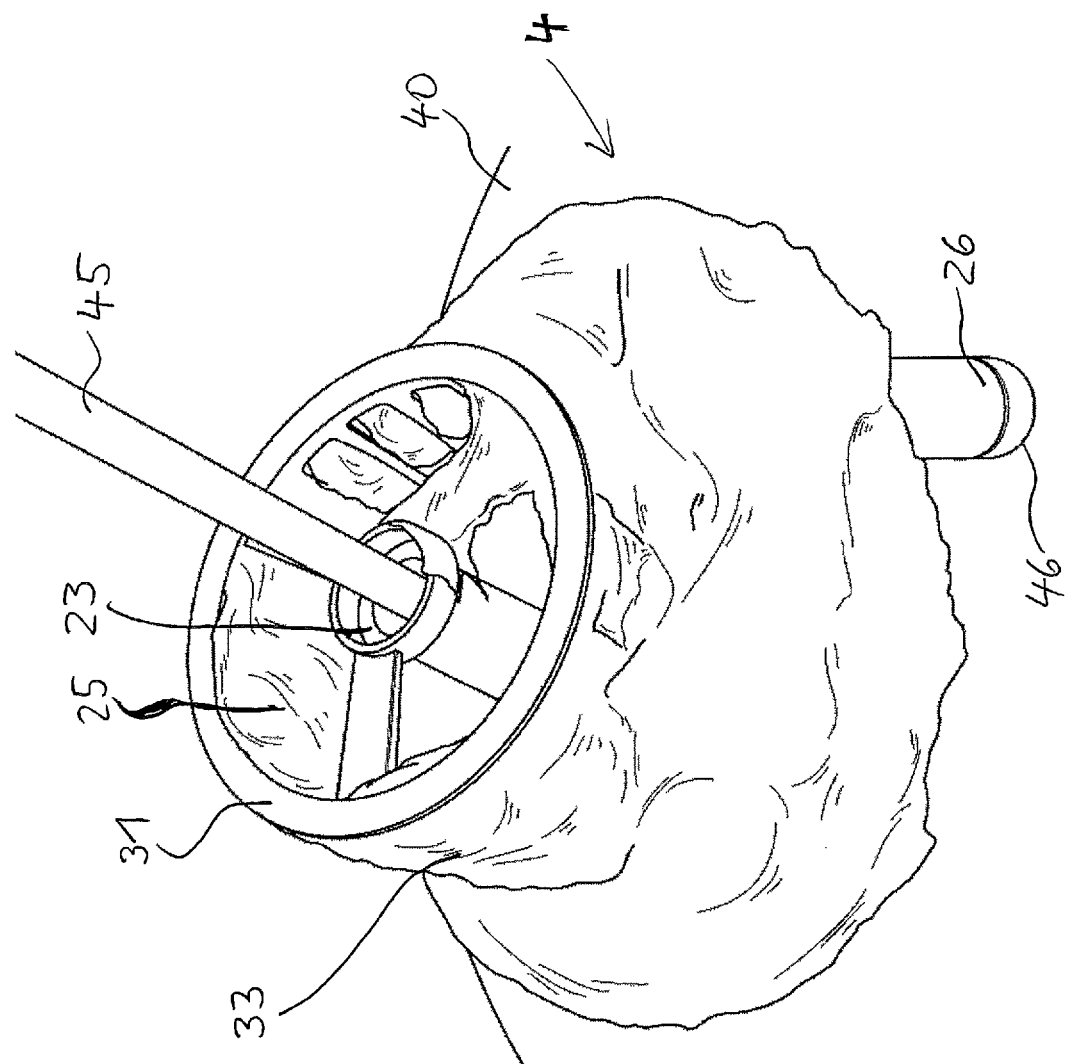

A second embodiment of the invention is depicted in FIGS. 6 to 8. The figures show the preparation of the surgical guidance device while the guiding system 2 is in the manufacturing system 4. For this purpose, the guiding system 2 with its guiding part 23 and its base module 20 is mounted via the mechanical interface to the holder 40. For example, the interface means can be established by a hemispherical connection between second interface means 26 of the base module 20 and third interface means 46 of the holder 40.

However, it is also possible to implement the elements of the mechanical interface which were explained before.

In the second embodiment, the connecting means 3 are not solely established by a modifiable material, as it was explained for the first embodiment. Instead, there are additional elements which allow for the required positioning and adjustment of the guiding part 23 relative to the base module 20. As an example, FIGS. 6 to 8 show an articulated mechanical connection part 30, 31, e.g. in the form of a ball socket/ball connection. In this way, an upper connection part 31 comprising the outer shape of a ball and a lower connection part 30 comprising a ball socket shape with the same diameter as a ball shape of the upper connection part 31. The lower connection part 30 is fixedly mounted on the base module 20 or may be rotatable and/or shiftable on the base module 20. It is also possible to provide the base module 20 as a one part device with the lower connection part 30.

The patient-specific adjustment procedure can be done in the same way as it was explained with regard to FIGS. 4 and 5. Therefore, the same type of manufacturing system 4 can be used. As an alternative to the two x-y-actuating units 43, 44, the holder 40 may be placed on a hexapod or Stewart platform actuator.

As can be seen in FIG. 7, a retaining part 45 is again ducted through the guidance channel 230 of the guiding part 23 for positioning and retaining the guiding part 23 in the patient-specific adjustment. The guiding part 23 may be axially moveable relative to the upper connection part 31, e.g. by means of a thread on the outside of the guiding part 23 and the inside of the upper connection part 31.

During the adjustment procedure or when the adjustment procedure is finished, the positioning achieved between the upper and the lower connection part 30, 31 and between the lower connection part 30 and the base module 20 can be fixated, e.g. by applying the modifiable material 33, as depicted in FIG. 8, or by applying any other chemical or non-chemical fixation means. For example, it is also possible to use fast curing glue, like CA glue, for doing the necessary fixation, or in other words for transforming the connecting means 3 from the non-fixed operating state (as depicted in FIGS. 6 and 7) into the fixed operating state.

The upper connecting part 31 may comprise a reception chamber 25 for reception of at least some of the modifiable material 33.

Figure 9:
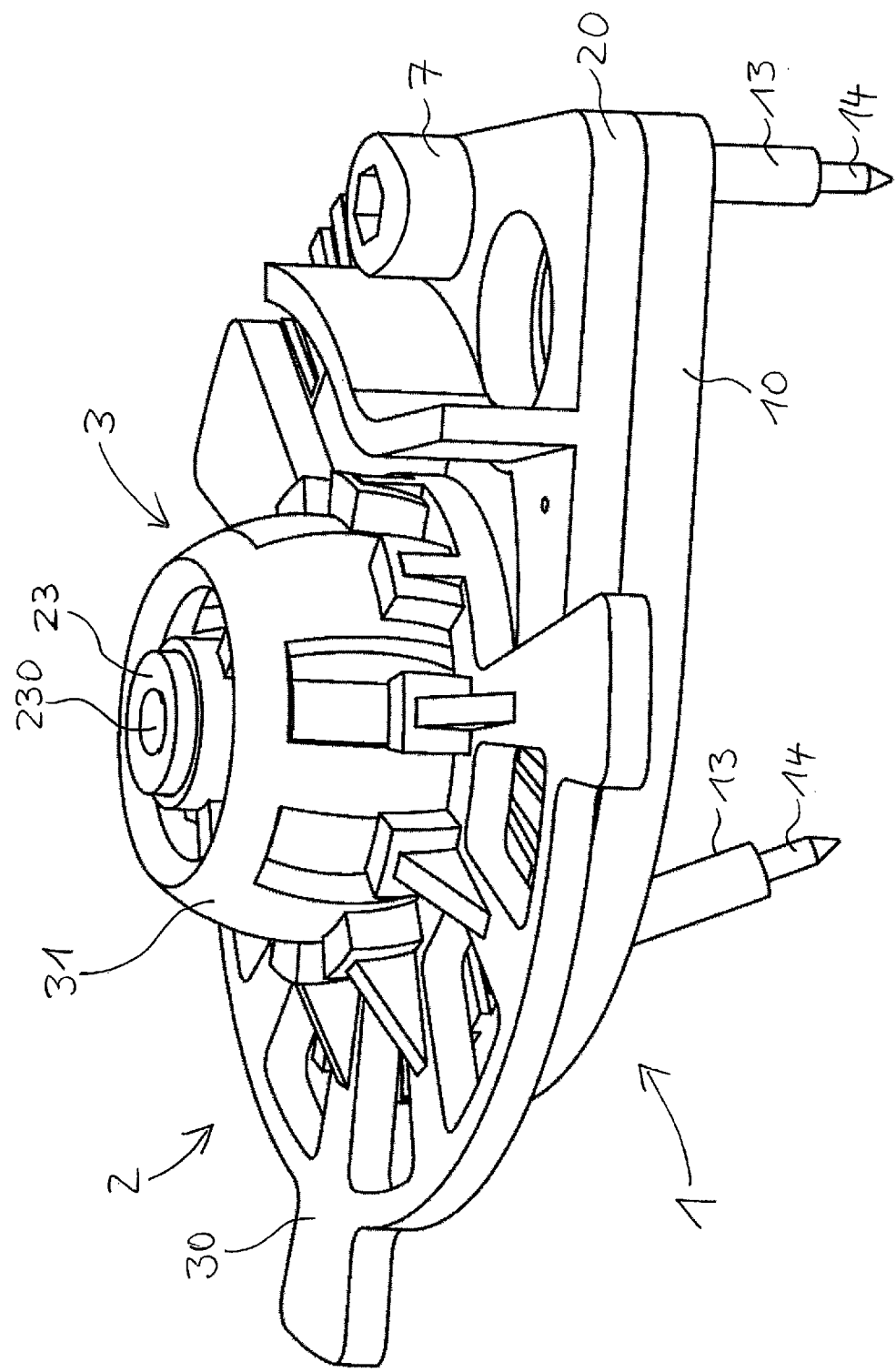

A third embodiment is depicted in FIGS. 9 to 16. The arrangement shown in FIG. 9 has several similarities to the second embodiment, therefore mainly the differences to that embodiment are pointed out. FIG. 9 shows the surgical guiding device with the carrier system 1 and the guiding system 2. The guiding system 2 again comprises, similarly to the second embodiment, a ball socket/ball-connection for providing connecting means 3 for establishing a mechanical connection between the guiding part 23 and the base module 20. For fixation and adjustment purposes, the guiding system 2 is screwed to the mounting structure 10 of the carrier system 1 via a screw 7.

Figure 10:
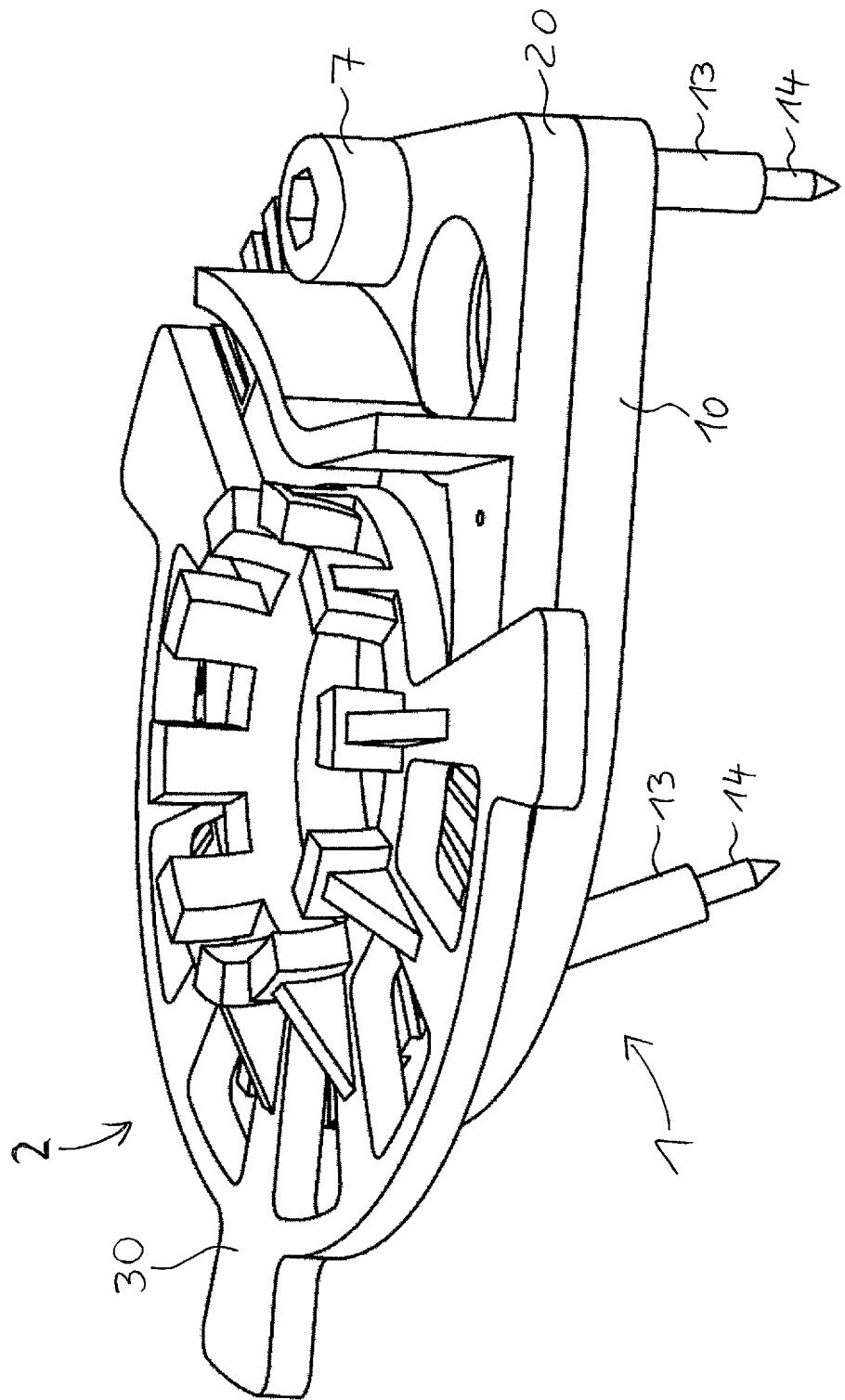
Figure 11:
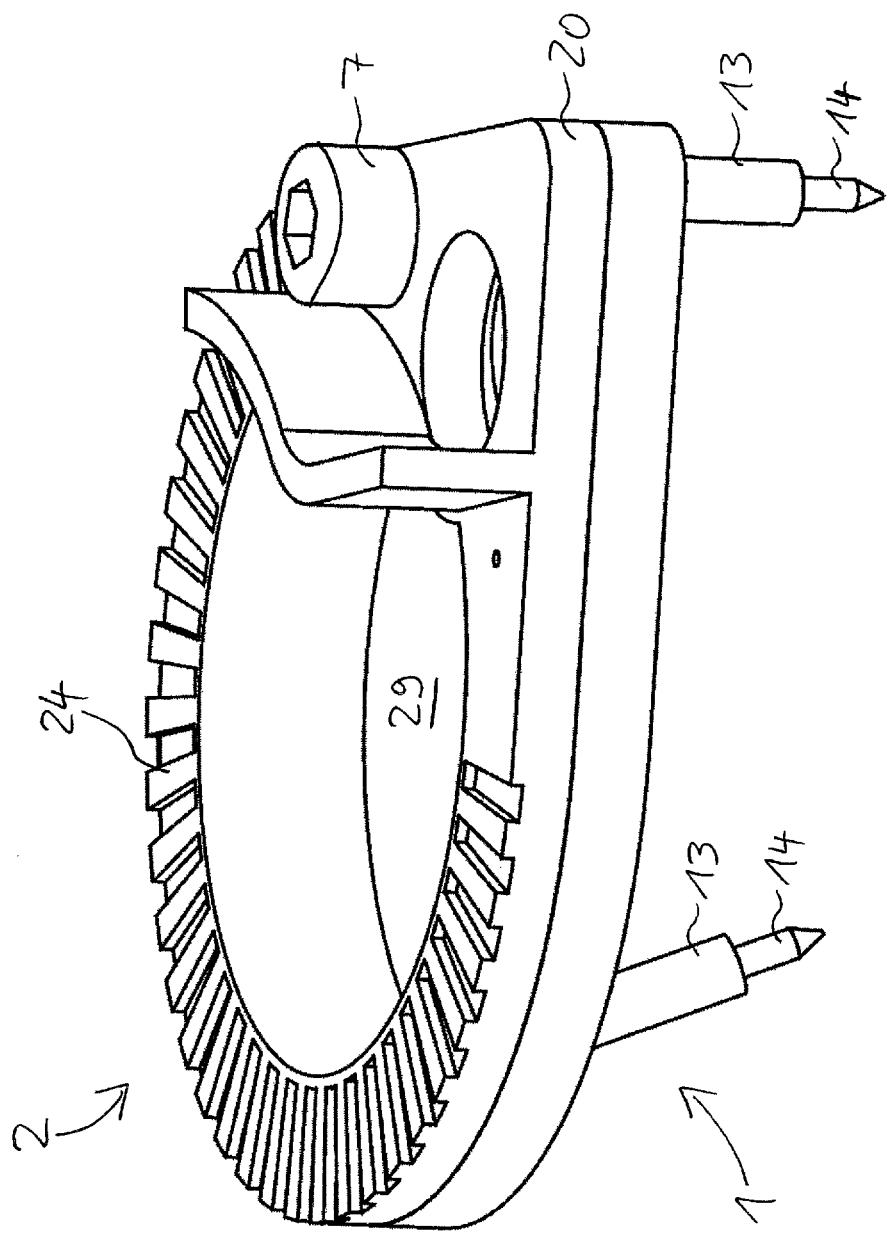

While FIG. 9 shows the complete surgical device (without manufacturing system), FIG. 10 shows the same device without the upper connecting part 31 and without the guiding part 23. In FIG. 11, also the lower connecting part 30 has been removed. As can be seen, there is a certain uneven surface structure 24 on the upper side of the base module 20, which is the contact surface for the lower connection part 30. The lower connection part 30 also comprises an uneven surface structure on its lower side. The lower connection part 30 can be shifted on the base module 20 as long as the connecting means are not in the fixed operating state. When the connecting means are in the fixed operating state, the uneven surface structure 24 is helpful for achieving a robust mechanical connection between the lower connection part 30 and the base module 2.

Figure 12:
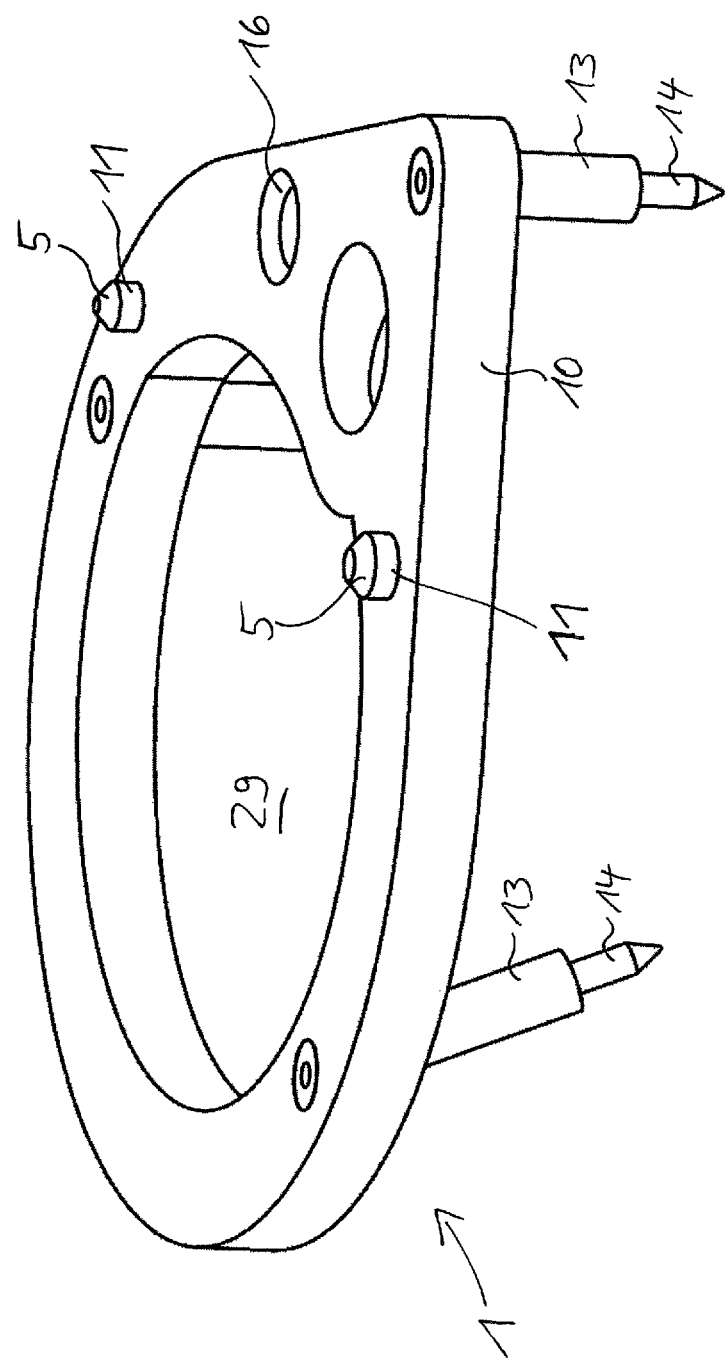

FIG. 12 shows only the carrier system 1, or in other words, compared to FIG. 11 the base module 20 has been removed. It can be seen that in this embodiment the carrier system 1 comprises third interface means 11 in the form of dowel pins and of an internal thread 16 for receiving the screw 7.

Figure 13:
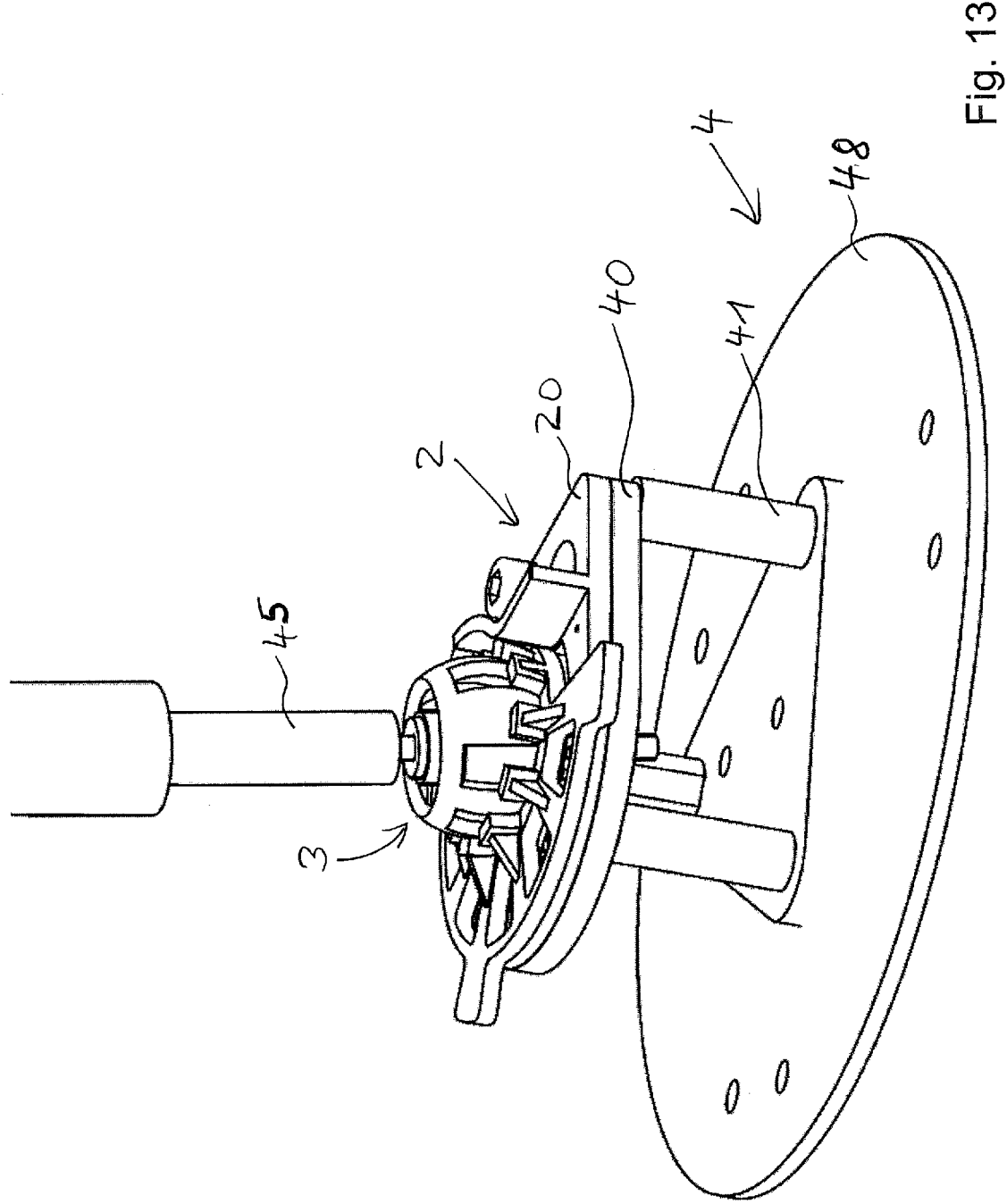

FIG. 13 shows how the patient-specific adjustment is reached using again a manufacturing system 4 of any of the aforementioned types. In the embodiment depicted in FIGS. 13 to 16, the manufacturing system 4 again comprises a holder 40 holding the base module 20 which is mechanically connected via a frame structure 41 to an support plate 48, which can be moved e.g. by a hexapod mounted below the support plate 48. Again the guiding part 23 is retained by a retaining part 45, as explained before.

Figure 14:
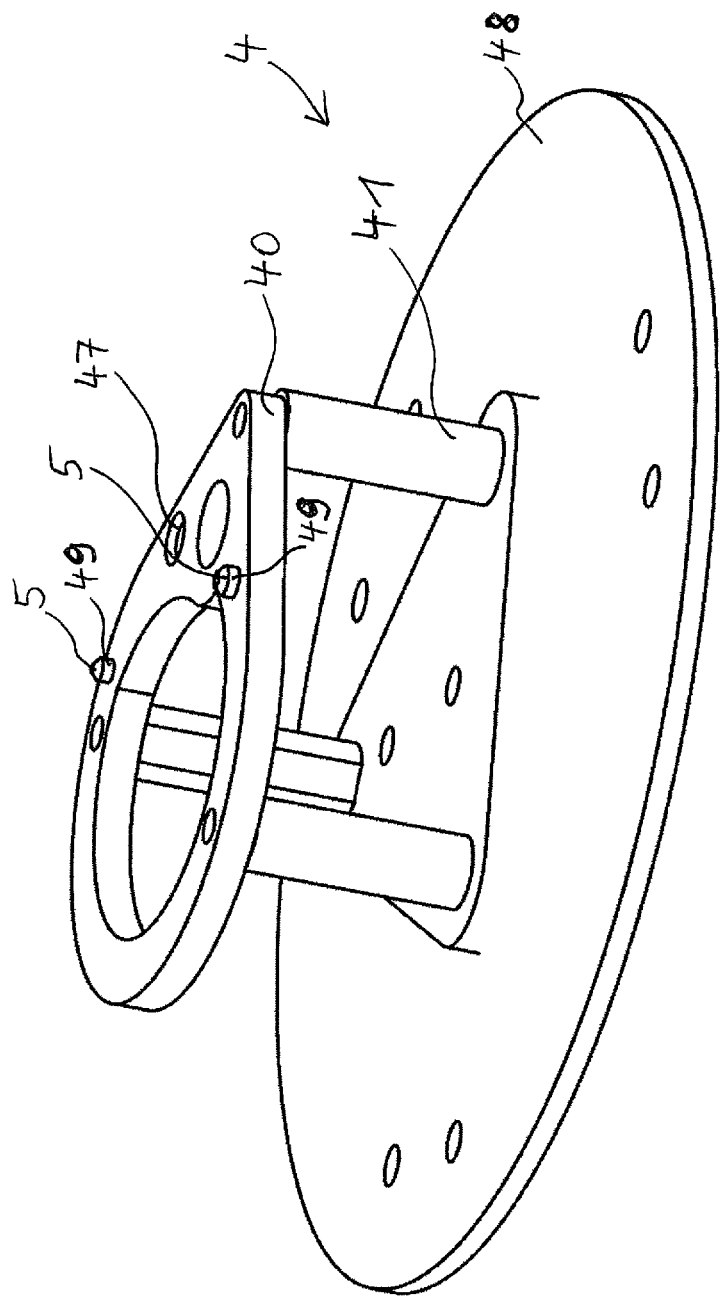
Figure 15:
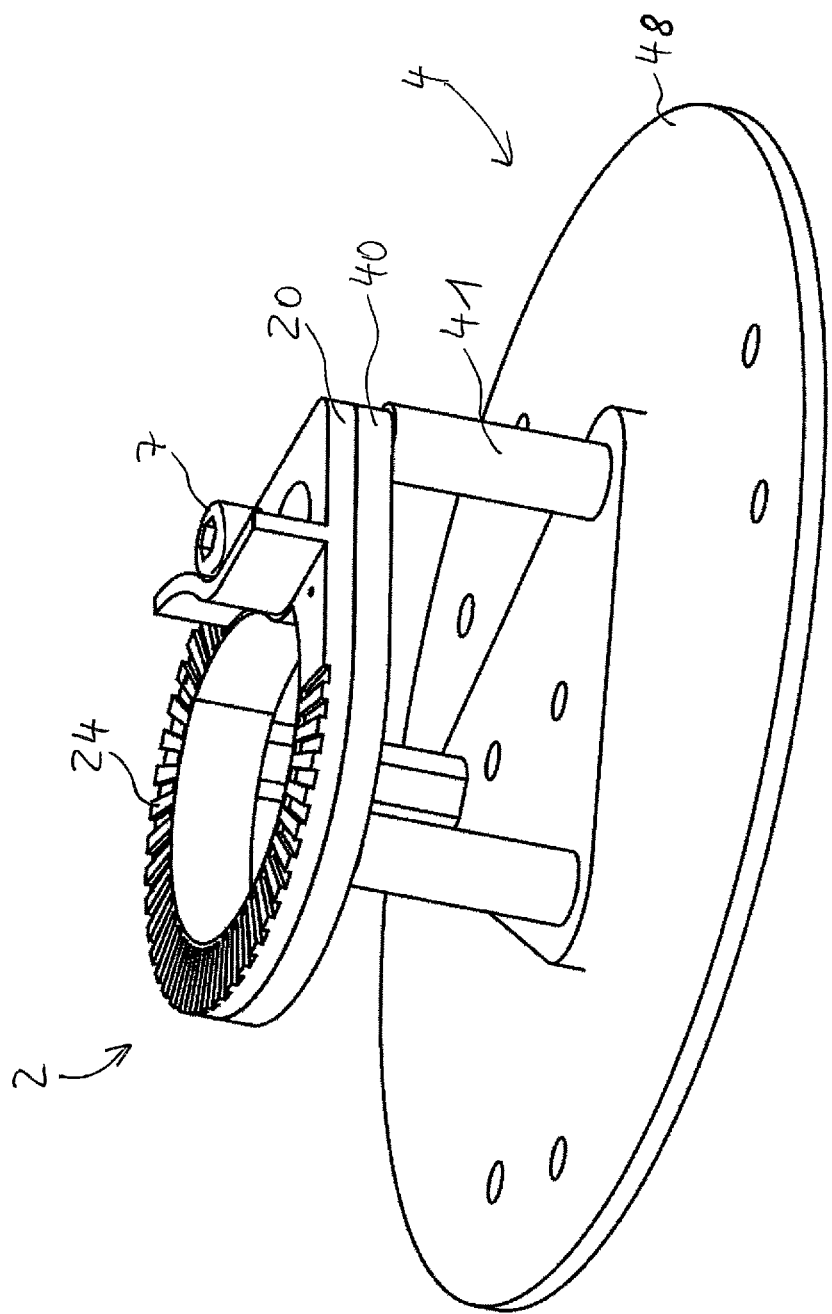
Figure 16:
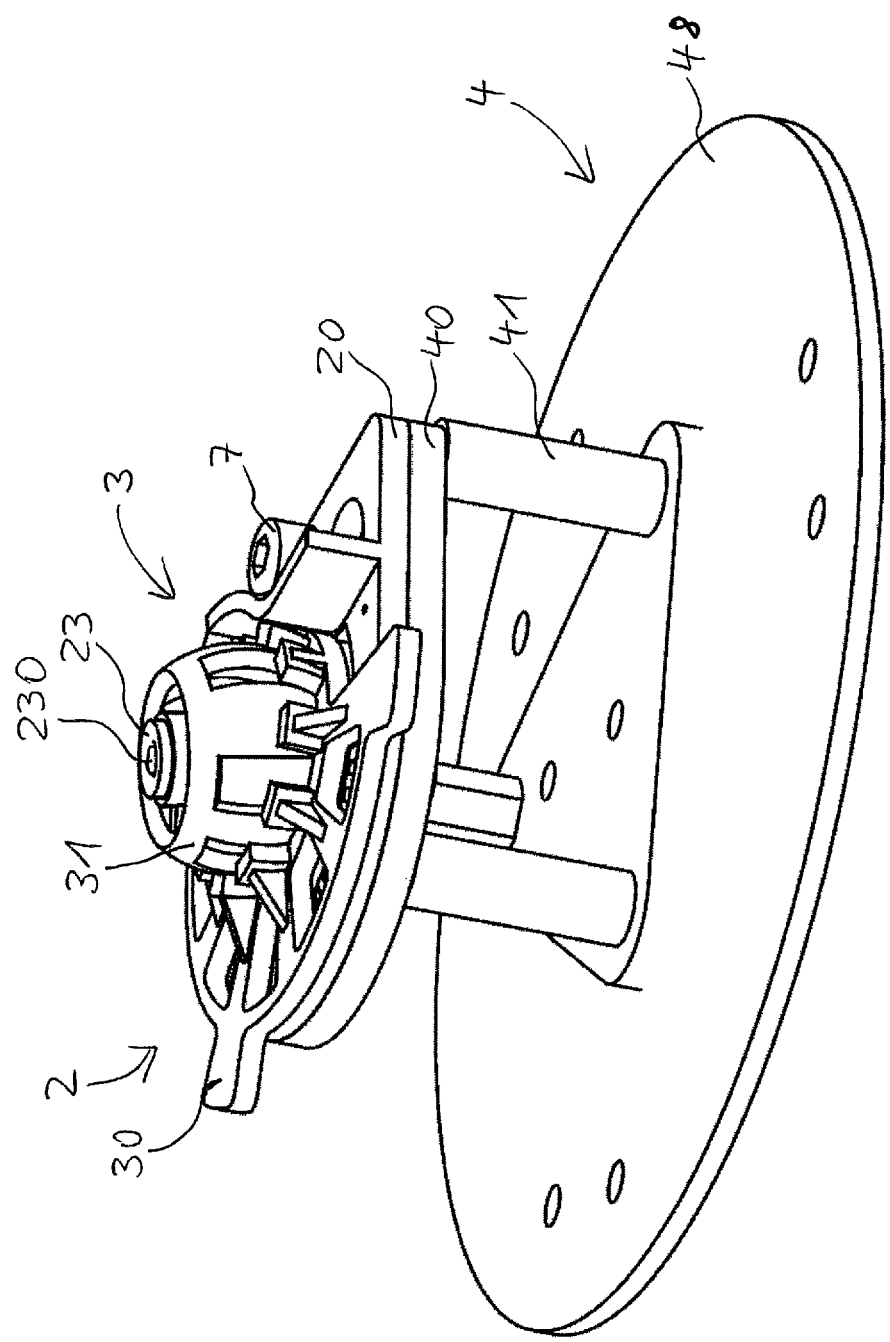

FIG. 14 shows the arrangement of FIG. 13 but without the guiding system 2 and the retaining part 45. FIG. 15 shows the arrangement of FIG. 14, wherein the base module 20 is mounted via the mechanical interface to the holder 40. In FIG. 16, the same arrangement as depicted in FIG. 13 is shown, but without the retaining part 45.

Figure 17:
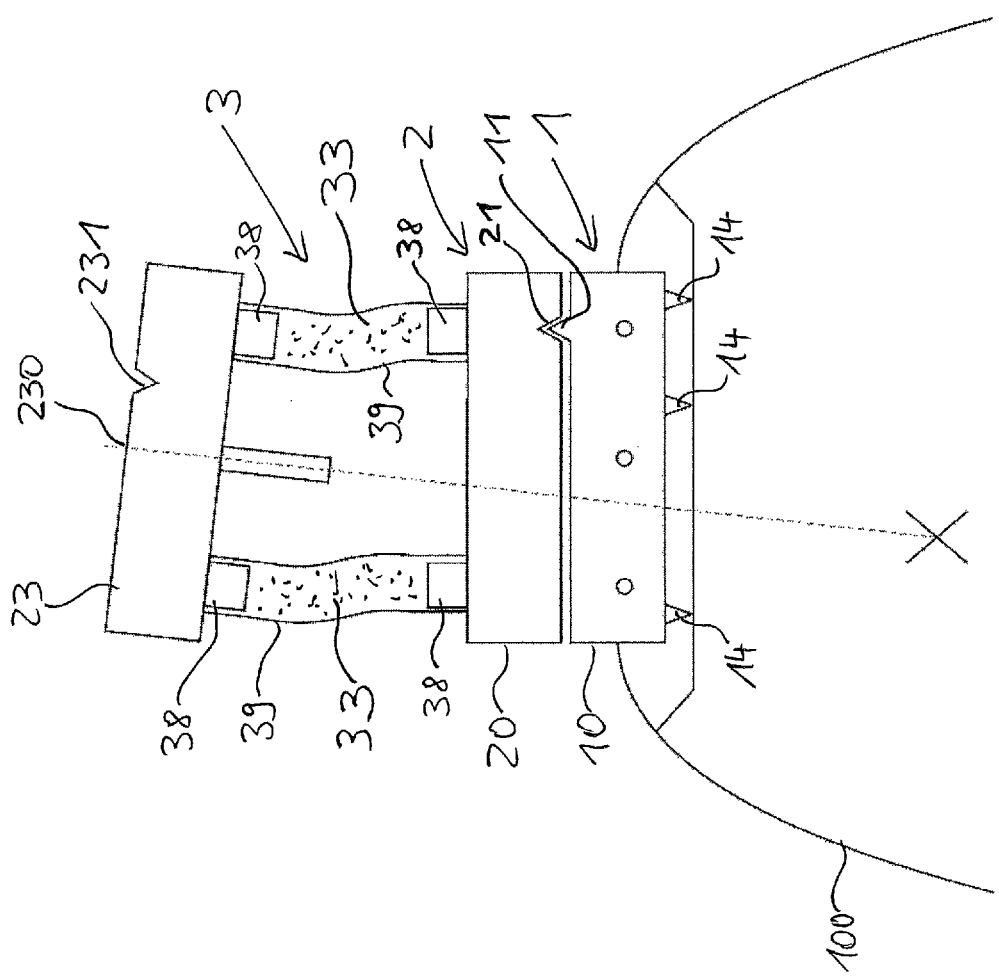
Figure 18:
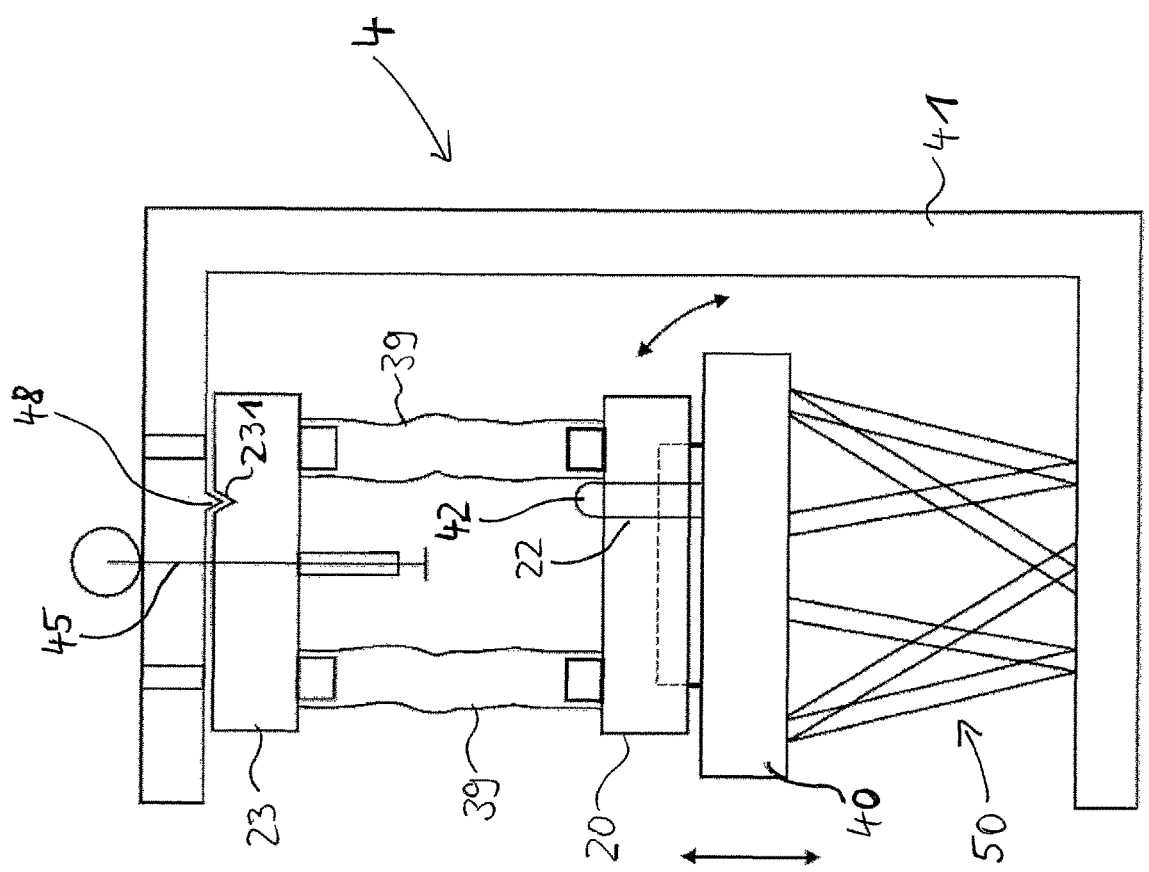
Figure 19:
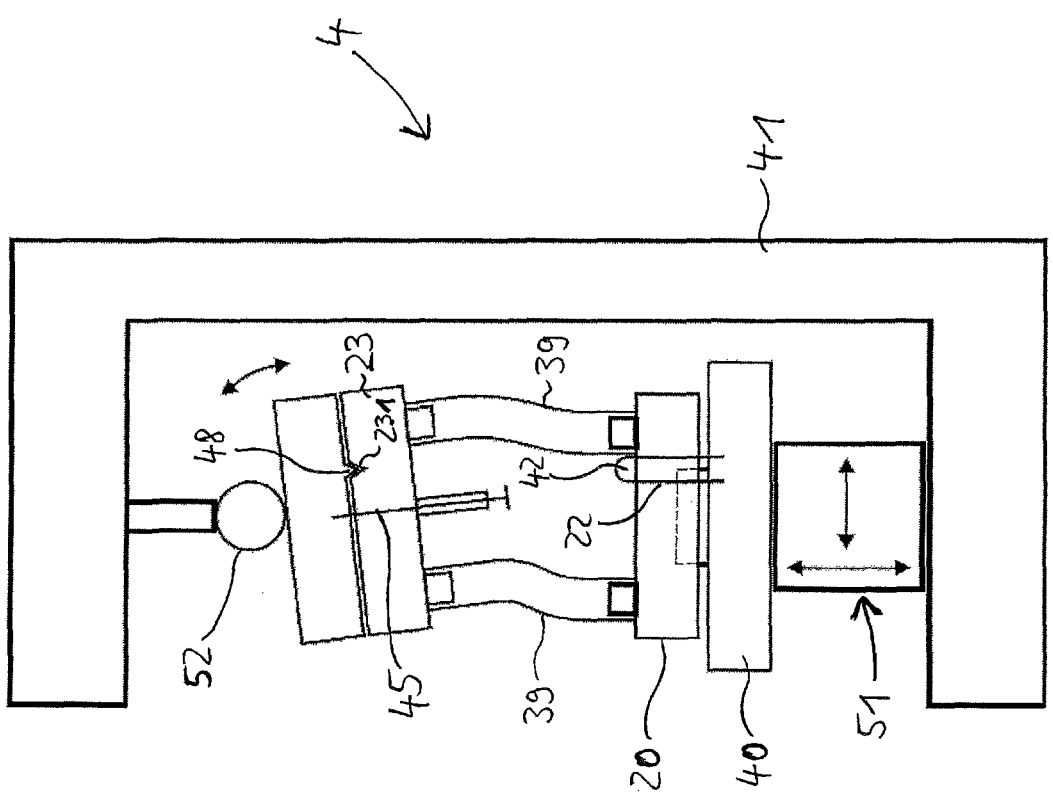

In the fourth embodiment of the invention, depicted in FIGS. 17 to 19, a different approach regarding the connection means is proposed. As can be seen in FIG. 17, which shows a surgical guidance device mounted to a bone structure 100 of a patient similarly to FIG. 1, the base module 20 is mechanically connected to the guiding part 23 by means of columnar structures. These columnar structures are established by flexible hoses 39 which are filled with the already mentioned modifiable material 33. Since the hoses 39 are very elastic, the adjustment of the guiding part 23 relative to the base module 20 can be easily modified as long as the modifiable material is not hardened. The hoses 39 are drawn over mounting sockets 38 located both on the guiding part 23 and the base module 20.

Similarly to the other embodiments, the base module 20 is connected with the carrier system 10 via a form fit connection through second interface means 21 and first interface means 11. In the embodiment shown in FIG. 17, one of the interface means can be formed like a spike, the other one like a notch having the complementary form of the spike.

FIG. 18 shows the preparation of the guiding system 2 within a manufacturing system 4. Again, the guiding system 2 is located within a frame 41 of the manufacturing system, and it is mounted via a form fit connection to a holder 40. The example depicted in FIG. 18 shows that the second interface means used for connecting the base module 20 to the holder 40 are not necessarily the same part of the second interface means as used for establishing the form fit connection of the base module 20 to the carrier system 10. Instead, another part of the second interface means 22, in this case a through hole in the plate like base module 20, can be used for establishing the form fit connection to the holder 40. In this case, the third inter-face means 42 are established by a bolt which is guided through the through hole in the base module 20.

Further, there is another form fit connection by additional interface means 48, 231 established between the guiding part 23 and an upper part of the frame 41 of the manufacturing system 4. This ensures that the guiding part 23 is held in a defined fixed position when the holder 40 is moved by an actuator of the manufacturing system 4, in order to achieve the patient-specific adjustment.

In the embodiment shown in FIG. 18 the actuator for actuating the holder 40 is a hexapod 50.

FIG. 19 shows the preparation of the guiding system 2 in a manufacturing system 4 which is different to the embodiment shown in FIG. 18. As a difference to FIG. 18, the embodiment of FIG. 19 comprises an actuator in the form of a three axis linear actuator 51, which allows movement of the holder 40 in three orthogonal spatial directions (x, y, z). In order to allow the guiding part 23 be located and adjusted in different angular positions relative to the base module 20, the guiding part 23 is mounted to an articulated joint 52, e.g. in the form of a globe joint or a cardanic joint.

When the desired patient-specific adjustment is reached, the modifiable material 33 is filled into the hoses 39 and is then hardened. It is also possible to fill the modifiable material 33 into the hoses at an earlier time, and then adjust the guiding system in the patient-specific adjustment. This adjusting procedure is possible as long as the modifiable material is not hardened, or at least not completely hardened. Then, when the patient-specific adjustment is reached, it is waited until the modifiable material is hardened in a way that it securely fixates the patient-specific adjustment of the guiding system 2. After that, the guiding system 2 can be used in a surgical intervention, e.g. in the form depicted in FIG. 17.

The invention claimed is:

1. A surgical guidance device for patient-specific guidance of at least one tool used during a surgical intervention, comprising:
   a) at least one carrier system arranged for fixation on a bone structure of a patient,
   b) at least one guiding system connectable to the at least one carrier system, the at least one guiding system comprising at least one base module and at least one guiding part for guidance of at least one tool used during the surgical intervention,
   c) at least one connecting means for establishing a mechanical connection between the at least one guiding part and the at least one base module, wherein the at least one connecting means comprises at least a non-fixed operating state and a fixed operating state, wherein in the non-fixed operating state the at least one guiding part can be adjusted relative to the at least one base module in a patient-specific adjustment and in the fixed operating state the at least one guiding part is mechanically fixated relative to the at least one base module in the patient-specific adjustment,
   d) at least one mechanical interface for connecting the at least one carrier system to the guiding system, comprising a first interface means of the at least one carrier system and a second interface means of the at least one guiding system, wherein the first interface means is connectable via form fit with the second interface means, at least in part, thereby ensuring a defined adjustment of the at least one guiding system relative to the at least one carrier system by means of a form fit;
   e) wherein the at least one connecting means comprises at least a modifiable material with figurine and/or plastic properties, which in the non-fixed operating state is manually deformable and allows a patient-specific adjustment of the at least one guiding part relative to the at least one base module, wherein the modifiable material is rapidly hardened and/or cured, for transforming the connecting means into the fixed operating state.

2. The surgical guidance device according to claim 1 wherein the at least one connecting means is irreversibly transformable from the non-fixed operating state into the fixed operating state.

3. The surgical guidance device according to claim 1 wherein the at least one guiding system comprises at least one reception chamber for reception of the modifiable material.

4. The surgical guidance device according to claim 1 wherein the at least one base module is connected via one or more deformable and/or flexible hose-like coupling means with the at least one guiding part, wherein an interior of one or more of the hose-like coupling means forms a reception chamber for reception of the modifiable material.

5. The surgical guidance device according to claim 1 wherein the at least one connecting means comprises an articulated mechanical connection part.

6. The surgical guidance device according to claim 5 wherein the articulated mechanical connection part freedom of movement of the at least one guiding part relative to the at least one base module by at least one or at least two degrees of freedom when the at least one connecting means is in the non-fixed operating state.

7. The surgical guidance device according to claim 1 wherein the at least one connecting means is transformable from the non-fixed operating state into the fixed operating state in less than one hour.

8. The surgical guidance device according to claim 1 wherein the at least one guiding part comprises a guiding channel for guiding a surgical drill or other medical instrument.

9. The surgical guidance device according to claim 1 further comprising a manufacturing system which comprises a holder for holding the at least one base module, wherein the holder comprises third interface means that is connectable via form fit to the second interface means, at least in part, thereby ensuring a defined adjustment of the at least one guiding system relative to the holder by means of form fit.

10. The surgical guidance device according to claim 9 wherein a manufacturing system comprises a retaining part for retaining the at least one guiding part.

11. The surgical guidance device according to claim 10 wherein the manufacturing system comprises an adjustable positioning means which allow adjustment of the retaining means and/or the holder relative to each other in order to adjust the at least one a guiding part retained by the retaining means relative to the at least one base module held by the holder in the desired patient-specific adjustment.

12. A method for preparation of a surgical guidance device for patient-specific guidance of at least one tool used during a surgical intervention, comprising: at least one carrier system arranged for fixation on a bone structure of a patient; at least one guiding system connectable to the at least one carrier system, the at least one guiding system comprising at least one base module and at least one guiding part for guidance of at least one tool used during the surgical intervention; at least one connecting means for establishing a mechanical connection between the at least one guiding part and the at least one base module, wherein the at least one connecting means comprises at least a non-fixed operating state and a fixed operating state, wherein in the non-fixed operating state the at least one guiding part can be adjusted relative to the at least one base module in a patient-specific adjustment and in the fixed operating state the at least one guiding part is mechanically fixated relative to the at least one base module in the patient-specific adjustment; and at least one mechanical interface for connecting the at least one carrier system to the guiding system, comprising a first interface means of the at least one carrier system and a second interface means of the at least one guiding system, wherein the first interface means is connectable via form fit with the second interface means, at least in part, thereby ensuring a defined adjustment of the at least one guiding system relative to the at least one carrier system by means of a form fit, comprising:
   adjusting intraoperatively the at least one guiding part relative to the at least one base module in the patient-specific adjustment; and
   fixating in the patient-specific adjustment through transforming the connecting means from the non-fixed operating state into the fixed operating state; and
   wherein the at least one connecting means comprises at least a modifiable material with figurine and/or plastic properties, which in the non-fixed operating state is manually deformable and allows a patient-specific adjustment of the at least one guiding part relative to the at least one base module, wherein the modifiable material is rapidly hardened and/or cured, for transforming the connecting means into the fixed operating state.

13. The method according to claim 12 wherein the at least one guiding part is adjusted relative to the at least one base module by means of a manufacturing system and is mechanically supported by the manufacturing system at least until the transforming of the at least one connecting means into the fixed operating state is finished to the extent that the at least one guiding part is fixated relative to the at least one base module in the patient-specific adjustment.

14. The method according to claim 13 further comprising the steps of:
   removing the at least one guiding system from the manufacturing system; and
   mounting the at least one guiding system to the at least one carrier system via the mechanical interface for connecting the at least one carrier system with the at least one guiding system after the at least one guiding part is fixated relative to the at least one base module in the patient-specific adjustment.

* * * * *